US00PP23587P2

(12) United States Plant Patent
Bergeron

(10) Patent No.: US PP23,587 P2
(45) Date of Patent: May 7, 2013

(54) ***HOSTA* PLANT NAMED 'AMERICAN HERO'**

(50) Latin Name: ***Hosta* hybrid (Tratt.)**
Varietal Denomination: American Hero

(75) Inventor: Amy Bergeron, Holland, MI (US)

(73) Assignee: Walters Gardens Inc., Zeeland, MI (US)

( * ) Notice: Subject to any disclaimer, the term of this patent is extended or adjusted under 35 U.S.C. 154(b) by 93 days.

(21) Appl. No.: 13/135,669

(22) Filed: Jul. 12, 2011

(51) Int. Cl.
*A01H 5/00* (2006.01)

(52) U.S. Cl. ..... Plt./353

(58) Field of Classification Search ..... Plt./353
See application file for complete search history.

*Primary Examiner* — June Hwu

(57) ABSTRACT

A new and unique *Hosta* plant named 'American Hero' characterized by compact plant habit and stiff, upright, heavily-substanced, twisted, variegated leaves with dark green margins and creamy centers. The leaf veins have an irregular and unusual fusing, a puckering or corrugation especially between the leaf margin and center and the creamy centers have an irregular green flecking. Flowering lasts for about 3 to 4 weeks beginning in mid-July with numerous light-lavender upward-facing flowers on cream-colored scapes.

1 Drawing Sheet

Botanical classification: *Hosta* hybrid (Tratt.)
Variety denomination: 'American Hero'.

BACKGROUND OF THE INVENTION

The present invention relates to the new and distinct *hosta* plant, *Hosta* 'American Hero' discovered by Amy Bergeron at a nursery in Zeeland, Mich., USA as an uninduced whole-plant mutation in a tissue cultured crop of *Hosta* 'Loyalist' (not patented) the summer of 2005. The new plant has been successfully asexually propagated both by division and by tissue culture at a nursery in Zeeland, Mich. Both methods of asexual propagation systems have been found produce stable and identical plants that maintain the unique characteristics of the original plant.

BRIEF SUMMARY OF THE INVENTION

*Hosta* 'American Hero' differs from its parent, 'Loyalist', as well as all other *hostas* known to the applicant. The most similar known *hosta* cultivars are: 'Americana' (not patented), 'Loyalist' (not patented), 'Revolution' (not patented), 'Paul Revere' (not patented), 'Fire and Ice' (not patented) and 'Pathfinder' (not patented). 'Loyalist', 'Fire and Ice' and 'Paul Revere' all appear to be identical to each other, but are independently derived sports all from 'Patriot' with flat leaves having a dark-green margin and white center having a small number of green speckles in the center. 'Revolution', 'Americana' and 'American Hero' are directly or indirectly sports (mutations) of 'Patriot' (not patented). All seven of the *Hosta* cultivars listed above have similar leaf variegation patterns with the green margins and whitish centers. *Hosta* 'American Hero' has a highly-contrasting, wide, deep-green leaf margins with a bright white leaf centers which have a unique speckling of green flecks of irregular lengths and widths. The new plant also has unique veining that produces an extreme twisting of the leaf blades.

TABLE 1

VARIEGATED HOSTA COMPARISON

| CULTIVAR | CENTER LEAF COLOR | MARGIN LEAF COLOR | SUBSTANCE |
|---|---|---|---|
| 'American Hero' | creamy white with green flecks | dark green | very high |
| 'Americana' | creamy white | dark green | high |
| 'Fire and Ice' | creamy white | dark green | high |
| 'Loyalist' | creamy white | dark green | moderate |
| 'Pathfinder' | creamy white with green flecks | dark green | moderate |
| 'Paul Revere' | creamy white with green flecks | dark green | moderate |
| 'Revolution' | creamy white with heavy green flecks | dark green | high |

The closest comparison variety is 'Revolution', and it differs primarily in that 'American Hero' has more twisted leaves with unusual fusing of veins. The new plant specifically differs from the parent 'Loyalist' in having heavier substance foliage, green flecking in the leaf center, more twisted foliage and an unusual fusing of the veins. *Hosta* 'American Hero' differs from all other *hostas* known to the applicant, by the combination of the following traits:

1. Compact plant habit with stiffly-upright, heavily-substance, twisted, variegated leaves with dark green margins and creamy centers having an irregular green flecking.
2. Light mint green scapes with upright facing buds and light lavender flowers beginning in mid July.
3. Primarily parallel veins with irregular fusing near the leaf edges.

BRIEF DESCRIPTION OF THE DRAWINGS

The photograph of the new plant demonstrates the overall appearance of the new plant including the unique traits as a three-year old plant grown in a container in a greenhouse with 50% shade and supplemental water and fertilizer as needed. The colors are as accurate as reasonably possible with color reproductions. Ambient light spectrum, temperature, source and direction may cause the appearance of minor variation in color.

FIG. 1 shows the new plant in a container.

DETAILED BOTANICAL DESCRIPTION

The following descriptions and color references are based on the 2001 edition of The Royal Horticultural Society Colour Chart except where common dictionary terms are used. The new plant, *Hosta* 'American Hero', has not been observed under all possible environments. The phenotype may vary slightly with different environmental conditions, such as temperature, light, fertility, moisture and maturity levels, but without any change in the genotype. The following observations and size descriptions are of a three-year old plant in a 50% shaded trial garden in Zeeland, Mich. with and supplemental water and fertilizer.

Botanical classification: *Hosta* hybrid (Tratt.).

Variety denomination: 'American Hero'.

Parentage: Uninduced whole-plant mutation of *Hosta* 'Loyalist'.

Propagation: Garden division and sterile plant tissue culture.

Time to initiate roots from tissue culture: About 18 days.

Growth rate: Moderate.

Crop time: About 12 weeks to finish during the summer in a 3.8 liter container from an established 2.5 cm tissue culture plug.

Rooting habit: Fleshy, lightly branching, with roots up to 25 cm long.

Plant shape and habit: Hardy herbaceous perennial with basal rosettes of leaves emerging from rhizomes, producing a symmetrical mound of distinctly upright leaves in youth, becoming slightly more horizontally mounded with age.

Plant size: Foliage height about 45 cm tall from soil line to the top of the leaves and about 55 cm wide at the widest point about 25 cm above soil line.

Foliage description: Cordate, acute leaf apex with cordate base.

Leaf blades: Simple, entire, puckered or corrugated especially in tissue between leaf center and margin; blade twisted; heavy substance or leaf thickness from upper to lower leaf surfaces; up to 18 cm long and 14 cm wide, average 15 cm long and 13 cm wide; usually bi-laterally symmetrical; glabrous and glaucous below, glabrous and shiny above; variegation pattern variable with the margin between about 5.5 cm to 2.0 cm wide in the blade center with some acute white points extending into the margin; dark green margin narrows near the apex to about 0.5 cm wide; flecks in the creamy-colored center vary in size from 2.0 cm long and 3.0 mm wide to 1.0 mm long and 0.5 mm wide with an average fleck about 2.0 mm long and 1.0 mm wide.

Leaf blade color:

*Adaxial (top) margin*.—Nearest RHS 139A upon emerging and mid-summer.

*Abaxial (bottom) margin*.—Nearest RHS 137B shortly after emerging and nearest RHS N138B mid-summer.

*Adaxial center*.—Between RHS 150D and RHS 154D with flecks of nearest RHS 137B and others lighter than RHS N138D shortly after emerging; by mid-summer the base color develops to lighter than RHS 155C with flecks of nearest RHS 139B, RHS 137A and lighter than RHS N138D.

*Abaxial center*.—Between RHS 150D and lighter than RHS 145D with flecks of RHS nearest RHS 145C and RHS 137C shortly after emerging; by mid-summer the base color develops to nearest RHS 155C with flecks of RHS 193A, RHS 137D and RHS 141C.

Petiole: Entire, glabrous; stiff; mostly straight from base of plant to leaf base, concave center about 7.0 mm deep; about 30.0 cm long and 1.0 cm wide at base; edge or margin of petiole with a green stripe, about 2 mm wide at base and 4 mm wide near blade.

Petiole color: Margin nearest RHS 139A and center nearest RHS 155A without green flecks.

Veins: Mostly parallel but often fusing near blade edge and tip; raised on abaxial side and impressed on adaxial surface; 9 to 10 pair.

Veins color: Same as surrounding leaf on both adaxial and adaxial sides and transition as leaf color through the season.

Flower description:

*Buds one day prior to opening*.—About 1.5 cm diameter at widest point and 6.0 cm long; globose center with acute and base narrowing to a diameter of about 4.0 mm in diameter.

*Bud color*.—Light lavender between RHS 85C and RHS 85D; terminal 1.0 mm to 2.0 mm of apex nearest RHS 139C.

*Flowers*.—Funnelform; with broadly flared tepals; 30 to 35 per scape; about 6.2 cm wide and 7.0 cm long, (distal flowers smaller), persists for a normal period, usually one day on plant or as cut flower; scapes remain effective with flowers from mid-July to mid-August; no detectable fragrance.

*Bracts*.—Each flower subtended by a single bract to 6.5 cm long and 2.0 cm wide decreasing in size distally; glaucous underneath, shiny above and glabrous both surfaces; margin entire, sessile with straight base, apex acute; concaved supporting flower bud; margin irregular, about 3.0 mm wide on largest bracts and decreasing proportionally on smaller bracts; center portion about 85% of total expanded width.

*Bract color*.—Adaxial margin nearest RHS 139A with an uneven or jagged inside border; Adaxial center nearest RHS 150D; Abaxial margin: mm wide margin of nearest RHS 136B; Adaxial center: nearest RHS 145D; All surfaces of bracts with tinting of nearest RHS N186C in form of tiny speckling concentrated in areas of more light exposure, especially distally; Veins: same color as surrounding tissue on adaxial and abaxial surfaces.

*Tepal*.—Two sets of three, fused at base; clavate with acute apex; glabrous, entire; approximately 6.0 cm long and 1.5 cm wide.

*Tepal color*.—Each set of three tepals colored independently; Outer set of three tepals: adaxial surface with base color of nearest RHS 76B with five veins of nearest RHS 76A and a thin margin of white (without tinting) at the basal ½ of the tepal; abaxial color nearest RHS 76D; Inner set of three tepals: adaxial surface with broad white (without tinting) margin of about 5.0 mm wide at center with a clear margin of about 2.0 mm extending distally starting in the center and extending to apex; center stripe of about 4.0 mm wide of between RHS 76A and RHS 76B; abaxial color nearest RHS 76D with a 2.0 mm clear margin starting at the middle and extending to the apex.

Gynoecium: Style: single, about 8.5 cm long, 1.0 mm diameter, curved upward at distal end a total of 90 degrees; color lighter near white, nearest RHS 155B; Stigma: globose, about 1.5 mm in diameter; near white, nearest RHS 155B.

Androecium: Filaments: six, about 1.0 mm in diameter and 6.8 cm long, curved upward distally a total of 90 degrees; near white, whiter than RHS 155D; Anthers: about 3.0 mm long and 1.0 mm wide; dorsifixed; dehiscent longitudinally; nearest RHS 158D; Pollen: elliptical, less than 0.1 mm long, nearest RHS 17A.

Peduncle: One per mature division; initially glaucous, becoming dull; glabrous; without vertical ridges; upright, usually to 90 degrees from horizontal; about 55 cm tall, and up to 8.0 mm in diameter at base; average size about 50.0 cm tall and 7.0 mm diameter; color between RHS 145D and RHS 150D with stippling nearest RHS N186C concentrated in areas of more light exposure, especially distally.

Pedicel: Approximately 6.0 mm long, 2.0 mm wide; straight; lighter than RHS 76D; Fruit: tri-loculicidal capsule, about 3.5 cm long and 8.0 mm diameter; while developing nearest RHS 145D with tinting nearest RHS N186C and when mature nearest RHS 164C.

Seed: Flattened single-winged nutlet with swollen embryo at one end; about 7.0 mm long, 2 mm wide and 1.5 mm thick at embryo; nearest RHS 202A.

Disease and pest resistance: *Hosta* 'American Hero' stands up and resists slug infestation better than most other *hosta* plants in garden situations but has not been observed to be resistant to other diseases common to *hostas* beyond normal. The plant grows best and shows best coloration with plenty of moisture, adequate drainage and light shade, but is able to tolerate some sun or drought when mature. Hardiness at least from USDA zone 3 through 9, and other disease resistance is typical of that of other *hostas*.

I claim:

1. A new and distinct cultivar of ornamental *Hosta* plant named 'American Hero' as herein described and illustrated, suitable as a potted plant, for the garden, and for cut flower or leaf arrangements.

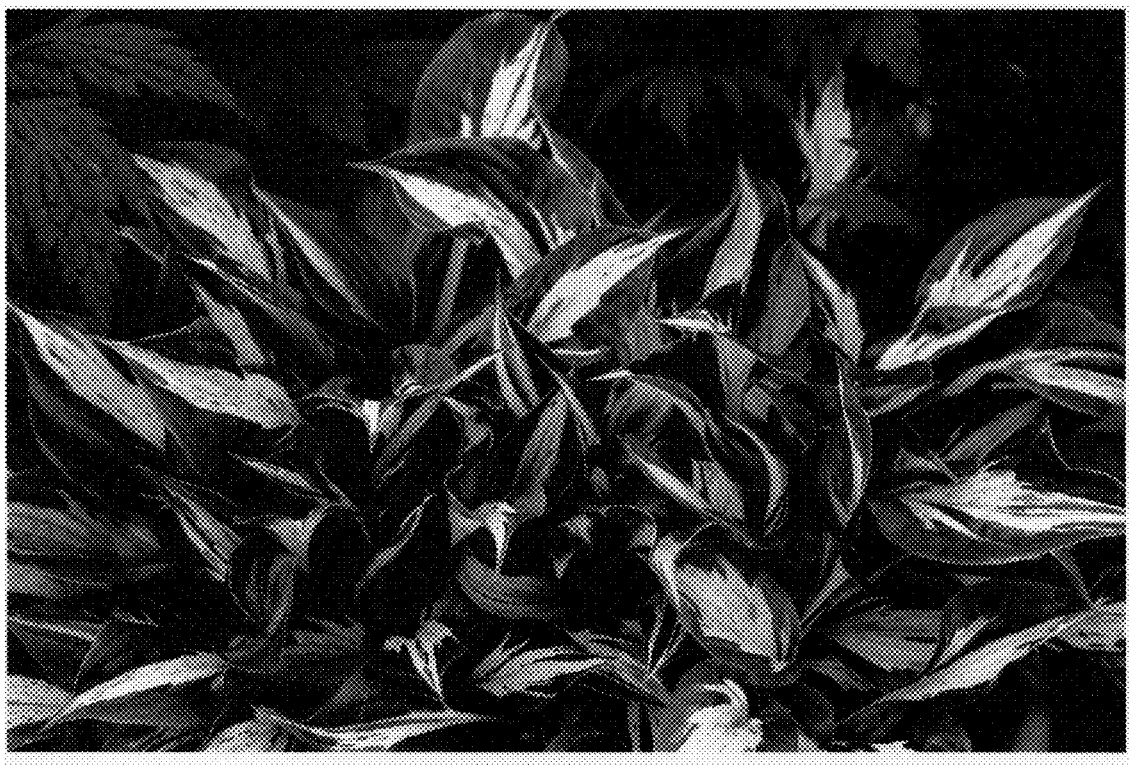

* * * * *